US009715219B2

(12) United States Patent
Koyama et al.

(10) Patent No.: US 9,715,219 B2
(45) Date of Patent: Jul. 25, 2017

(54) INFORMATION PROCESSING APPARATUS, INFORMATION PROCESSING METHOD, AND PROGRAM

(71) Applicant: Sony Corporation, Tokyo (JP)

(72) Inventors: Yuichiro Koyama, Tokyo (JP); Takeshi Asakawa, Chiba (JP); Shinako Matsuyama, Tokyo (JP)

(73) Assignee: Sony Corporation, Tokyo (JP)

( * ) Notice: Subject to any disclaimer, the term of this patent is extended or adjusted under 35 U.S.C. 154(b) by 7 days.

(21) Appl. No.: 13/779,873

(22) Filed: Feb. 28, 2013

(65) Prior Publication Data

US 2013/0258818 A1 Oct. 3, 2013

(30) Foreign Application Priority Data

Mar. 30, 2012 (JP) ................................. 2012-080995

(51) Int. Cl.
*G04G 21/00* (2010.01)
*G04G 99/00* (2010.01)
*A61B 5/16* (2006.01)
*G06Q 10/06* (2012.01)

(52) U.S. Cl.
CPC ............. *G04G 99/006* (2013.01); *A61B 5/16* (2013.01); *G04G 21/00* (2013.01); *G04G 99/00* (2013.01); *G06Q 10/06314* (2013.01)

(58) Field of Classification Search
CPC ...... G04G 21/00; G04G 99/00; G04G 99/006; A61B 5/00; A61B 5/16; G06Q 10/06314
USPC .................................... 368/34, 107, 250, 256
See application file for complete search history.

(56) References Cited

U.S. PATENT DOCUMENTS

| 5,006,985 A * | 4/1991 | Ehret et al. ..................... 705/1.1 |
| 5,970,468 A * | 10/1999 | Bull ................. G06Q 10/06311 705/32 |
| 6,119,095 A * | 9/2000 | Morita ................. G01C 21/343 705/5 |
| 6,304,519 B1 * | 10/2001 | Druk ........................ A61B 5/16 368/107 |
| 8,295,126 B2 * | 10/2012 | Wood .................... G04G 9/0076 368/21 |
| 8,762,190 B1 * | 6/2014 | Solomon .......... G06Q 10/06311 705/7.12 |
| 8,819,573 B2 * | 8/2014 | Chakra .............. G06Q 10/1093 368/21 |
| 2003/0129574 A1 * | 7/2003 | Ferriol et al. ................. 434/362 |

(Continued)

FOREIGN PATENT DOCUMENTS

JP 05-015595 A 1/1993

*Primary Examiner* — Amy Cohen Johnson
*Assistant Examiner* — Daniel Wicklund
(74) *Attorney, Agent, or Firm* — Chip Law Group

(57) ABSTRACT

There is provided an information processing apparatus, including a first information acquisition section which acquires priority action information, a second information acquisition section which acquires biological information related to a body clock of the user at a present time, a state setting section which sets an ideal state of the body clock corresponding to the priority action, a state estimation section which estimates a present state of the body clock at the present time, a third information acquisition section which acquires set action information related to a set action, and a display control section which displays a state of the body clock in the schedule on a display section.

13 Claims, 13 Drawing Sheets

(56) References Cited

U.S. PATENT DOCUMENTS

| | | | |
|---|---|---|---|
| 2004/0034289 A1* | 2/2004 | Teller et al. | 600/300 |
| 2005/0033122 A1* | 2/2005 | Balkin et al. | 600/300 |
| 2005/0177031 A1* | 8/2005 | Hursh | 600/300 |
| 2011/0015495 A1* | 1/2011 | Dothie et al. | 600/300 |
| 2011/0170379 A1* | 7/2011 | Eylon-Azoulay | G04G 9/02 368/15 |
| 2012/0078063 A1* | 3/2012 | Moore-Ede | B60K 28/06 600/300 |
| 2014/0149896 A1* | 5/2014 | Los | G06Q 10/1095 715/764 |

\* cited by examiner

FIG. 2

| TIME | JANUARY 1 | JANUARY 2 | JANUARY 3 | JANUARY 4 | JANUARY 5 | JANUARY 6 | JANUARY 7 |
|---|---|---|---|---|---|---|---|
| 0:00 | ▨ | ▨ | ▨ | ▨ | ▨ | ▨ | ▨ |
| 1:00 | ▨ | ▨ | ▨ | ▨ | ▨ | ▨ | ▨ |
| 2:00 | ▨ | ▨ | ▨ | ▨ | ▨ | ▨ | ▨ |
| 3:00 | ▨ | ▨ | ▨ | ▨ | ▨ | ▨ | ▨ |
| 4:00 | ▨ | ▨ | ▨ | ▨ | ▨ | ▨ | ▨ |
| 5:00 | ▨ | ▨ | ▨ | ▨ | ▨ | ▨ | ▨ |
| 6:00 | ▨ | ▨ | ▨ | ▨ | ▨ | ▨ | ▨ |
| 7:00 | | | | | | | |
| 8:00 | | | | | | | |
| 9:00 | | | | | | | |
| 10:00 | | | | | | | |
| 11:00 | | | | | | | |
| 12:00 | | | | | | | |
| 13:00 | | | | | | | |
| 14:00 | | | | | | | |
| 15:00 | | | | | | | |
| 16:00 | | | | | | | |
| 17:00 | | | | | | | |
| 18:00 | | | | | | | |
| 19:00 | | | | | | | |
| 20:00 | | | | | | | |
| 21:00 | | | | | | | |
| 22:00 | | | | | | | |
| 23:00 | | | | | | | |

▨ SLEEPING (a)

ACTION SELECTION SCREEN

☑ EATING  ☑ BASKING IN LIGHT

☐ SLEEPING  ☐ STUDYING

☐ WORKING  ☐ DRINKING

☑ SPORTS  ☐ ADMINISTERING MEDICATION

☐ TAKING EXAM

INFORMATION PROCESSING APPARATUS, INFORMATION PROCESSING METHOD, AND PROGRAM

BACKGROUND

The present disclosure relates to an information processing apparatus, an information processing method, and a program.

In recent years, attention has been drawn to the relationship between a person's body clock and his or her health. For example, it is known that disorders of the body clock provide adverse effects to the body, such as an increased risk of cancer. This is a major problem for people who may have an unsteady lifestyle, such as shift workers. Accordingly, in the case where the body clock is prevented from being shifted or the body clock is unavoidably shifted, it may be necessary to shift the body clock so as to suppress a burden on the body.

On the other hand, it has been understood that an appropriate time exists for many actions. For example, it has been understood that time zones exist, where psychiatric activities can be efficiently performed and where performance in sports can be improved.

JP H05-15595A discloses a system which controls biological rhythm by measuring the biological rhythm and adding an appropriate external stimulus. A method is disclosed in this system which adjusts a circadian rhythm in accordance with a working system and a time difference, or realizes an optimum awakening level which matches a target to a time during the day of an important sports game or business negotiation.

SUMMARY

Incidentally, implementation of a program is requested in which a user appropriately performs actions from a predetermined schedule by effectively utilizing his or her body clock. However, JP H05-15595A described above does not pay any attention whatsoever to controlling the body clock based on a real life schedule.

Accordingly, the present disclosure proposes a method in which a user appropriately performs actions from a predetermined schedule by effectively utilizing his or her body clock.

According to an embodiment of the present disclosure, there is provided an information processing apparatus, including a first information acquisition section which acquires priority action information associating a priority action of a user with a time when the priority action is performed, a second information acquisition section which acquires biological information related to a body clock of the user at a present time, a state setting section which sets an ideal state of the body clock corresponding to the priority action, based on the acquired priority action information, a state estimation section which estimates a present state of the body clock at the present time, based on the acquired biological information, a third information acquisition section which acquires set action information related to a set action that is included in a schedule of the user and is capable of being set at a given time, and a display control section which displays a state of the body clock in the schedule on a display section, based on a target value for displacing a phase of the body clock of the present state to a phase of the ideal state and the acquired set action information.

Further, according to an embodiment of the present disclosure, there is provided an information processing method, including acquiring priority action information associating a priority action of a user with a time when the priority action is performed, acquiring biological information related to a body clock of the user at a present time, setting an ideal state of the body clock corresponding to the priority action, based on the acquired priority action information, estimating a present state of the body clock at the present time, based on the acquired biological information, acquiring set action information related to a set action that is included in a schedule of the user and is capable of being set at a given time, and displaying a state of the body clock in the schedule on a display section, based on a target value for displacing a phase of the body clock of the present state to a phase of the ideal state and the acquired set action information.

Further, according to an embodiment of the present disclosure, there is provided a program for causing a computer to execute acquiring priority action information associating a priority action of a user with a time when the priority action is performed, acquiring biological information related to a body clock of the user at a present time, setting an ideal state of the body clock corresponding to the priority action, based on the acquired priority action information, estimating a present state of the body clock at the present time, based on the acquired biological information, acquiring set action information related to a set action that is included in a schedule of the user and is capable of being set at a given time, and displaying a state of the body clock in the schedule on a display section, based on a target value for displacing a phase of the body clock of the present state to a phase of the ideal state and the acquired set action information.

According to the embodiments of the present disclosure described above, it is possible for a user to appropriately perform actions from a predetermined schedule by effectively utilizing his or her body clock.

BRIEF DESCRIPTION OF THE DRAWINGS

FIG. 2 is a schematic diagram which shows an example of priority action information, which the user has input on an input screen, according to the embodiments of the present disclosure;

FIG. 10 is a figure which shows an example of set actions, which the user has selected on a selection screen, according to the embodiments of the present disclosure;

DETAILED DESCRIPTION OF THE EMBODIMENT(S)

Figure 1:
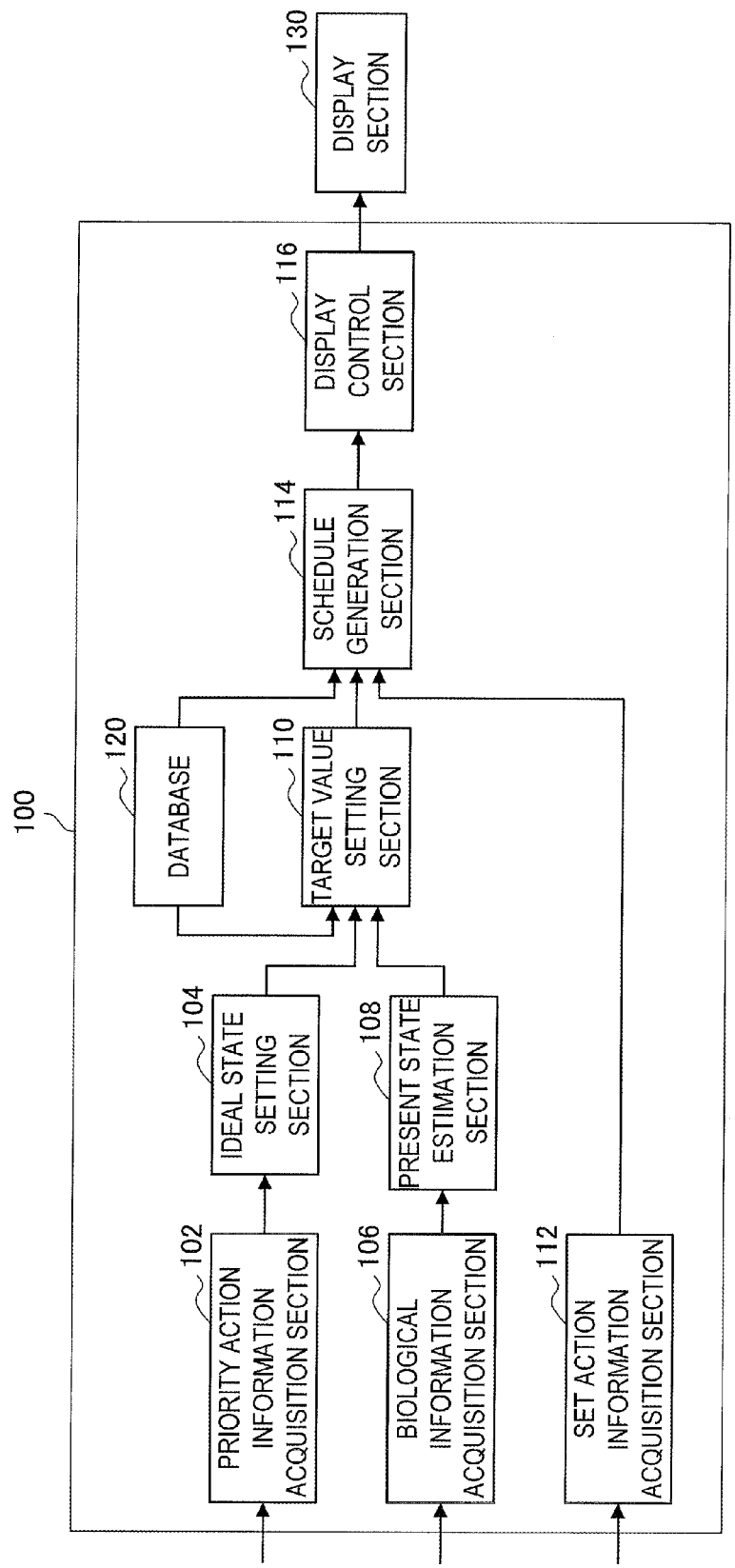
FIG. 1 is a figure which shows an example of a functional configuration of the information processing apparatus 100 according to the embodiments of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be given in the following order.

1. Configuration example of the information processing apparatus
2. Operation example of the information processing apparatus
3. Hardware configuration
4. Conclusion 1. \<Configuration Example of the Information Processing Apparatus>

A configuration example of an information processing apparatus 100 according to the embodiments of the present disclosure will be described with reference to FIG. 1. FIG. 1 is a figure which shows an example of a functional configuration of the information processing apparatus 100 according to the embodiments of the present disclosure.

The information processing apparatus 100 is a portable terminal such as a smart phone or a mobile phone, for example. As shown in FIG. 1, the information processing apparatus 100 has a priority action information acquisition section 102 which is an example of a first information acquisition section, an ideal state setting section 104, a biological information acquisition section 106 which is an example of a second information acquisition section, and a present state estimation section 108. In addition, the information processing apparatus 100 has a target value setting section 110, a set action information acquisition section 112 which is an example of a third information acquisition section, a schedule generation section 114, and a display control section 116.

(Priority Action Information Acquisition Section 102)

The priority action information acquisition section 102 acquires priority action information related to actions which have a high priority for the user. The priority action information is information which associates priority actions which have a high priority for the user with the times when the priority actions are performed. A priority action has the meaning of an action or the like in daily life, such as eating, sleeping, working, playing sports, taking an exam, basking in light, studying, drinking, or administering medication. Note that the priority action is not limited to those described above, and may include other various actions in the daily life of the user. Further, the priority action may further subdivide the above described actions. It is possible for the priority action information to be input by a user on an input screen, for example.

FIG. 2 is a schematic diagram which shows an example of priority action information, which the user has input on an input screen, according to the embodiments of the present disclosure. In FIG. 2, sleep is input as a priority action with a high priority between 12 AM and 7 AM for each day between January 1 and January 7. The type of priority action and the set time will differ depending on the user. Accordingly, FIG. 2 is merely an example, and the priority action information may be input such as shown in FIG. 3 or FIG. 4, for example.

Figure 3:
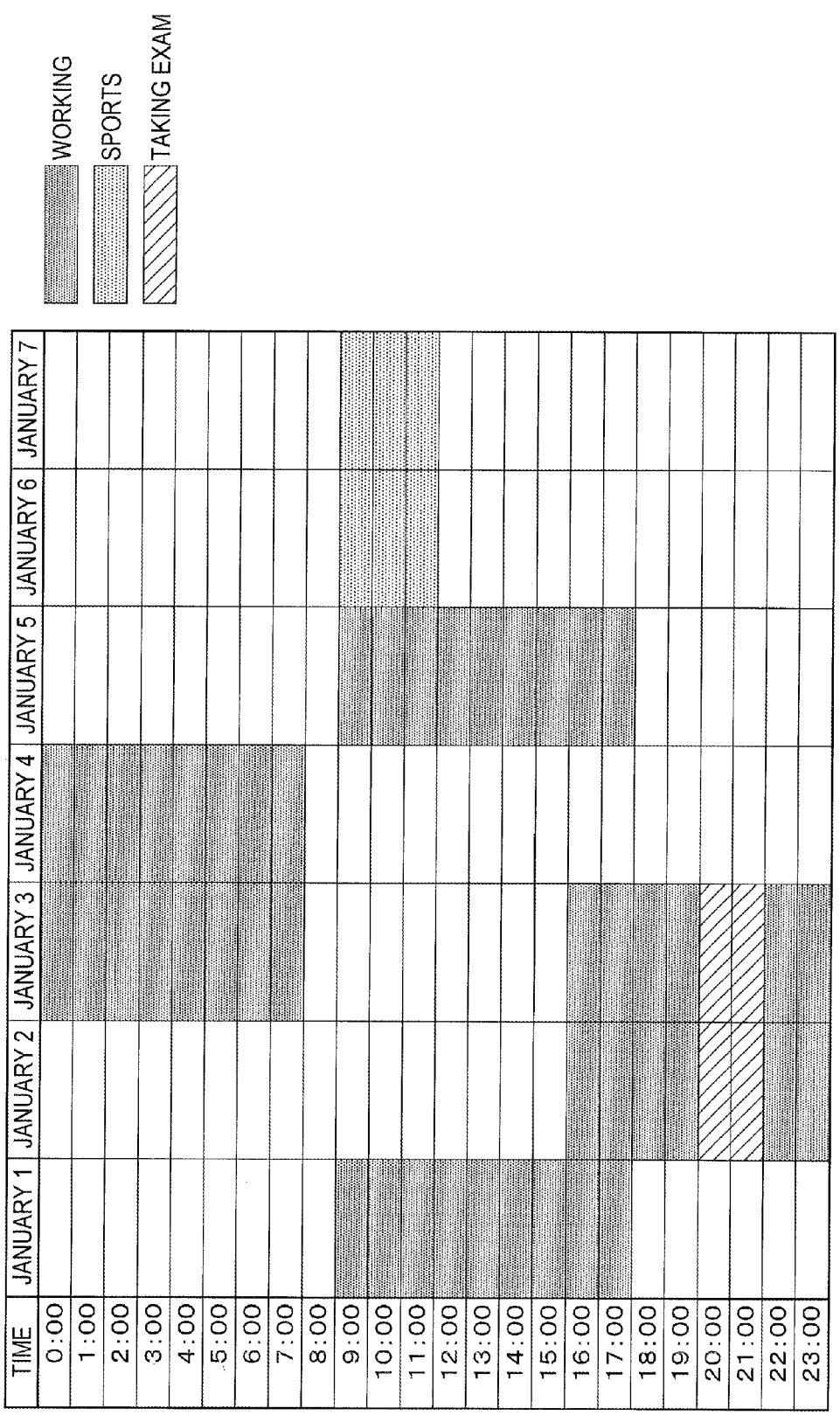
FIG. 3 is a schematic diagram which shows an example of priority action information, which the user has input on an input screen, according to the embodiments of the present disclosure.

FIG. 3 is a schematic diagram which shows an example of priority action information, which the user has input on an input screen, according to the embodiments of the present disclosure. The user who inputs the priority action information shown in FIG. 3 corresponds, for example, to a shift worker who works at a factory or the like. Working, taking an exam and sports are input as priority actions. When viewing the input priority action information, there are important exams on the nights of January 2 and January 3, and it can be presumed that the user enjoys playing sports on the weekend.

Figure 4:
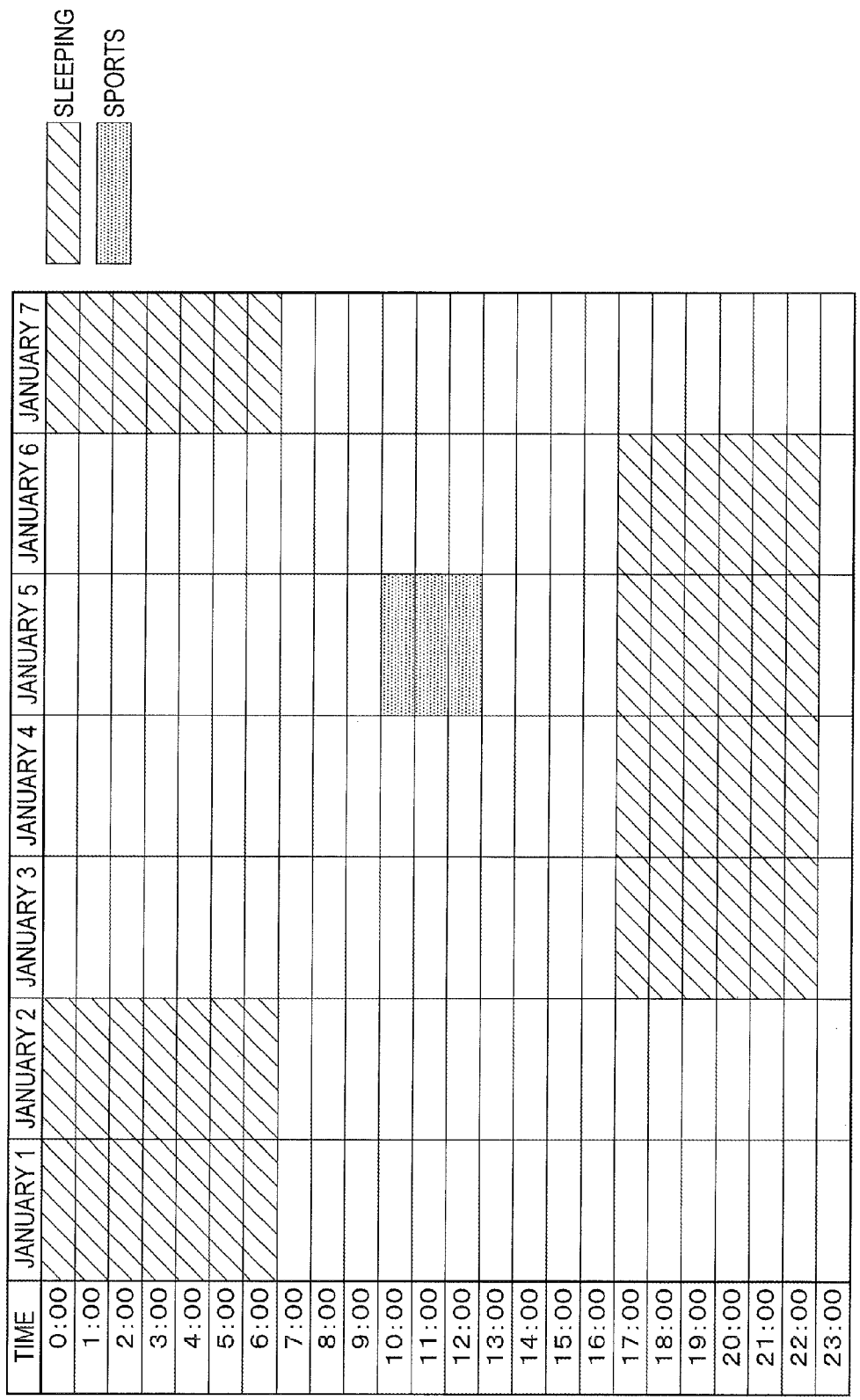
FIG. 4 is a schematic diagram which shows an example of priority action information, which the user has input on an input screen, according to the embodiments of the present disclosure.

FIG. 4 is a schematic diagram which shows an example of priority action information, which the user has input on an input screen, according to the embodiments of the present disclosure. The user who inputs the priority action information shown in FIG. 4 is, for example, an athlete. Sleeping and sports are input as priority actions. When viewing the input priority action information, it can be presumed that the user is preparing for an important game overseas on January 5.

The priority action information acquisition section 102 outputs the priority action information, acquired based on the input of the user, to the ideal state setting section 104. Note that while the above description has described the case where an input example of the priority action information is input in time units as shown in FIGS. 2 to 4, it is not limited to this. Further, the input screen is not limited to the display modes as shown in FIGS. 2 to 4.

(Ideal State Setting Section 104)

The ideal state setting section 104 sets the state of the user's ideal body clock according to the priority actions, based on the priority action information acquired from the priority action information acquisition section 102. In the biological rhythm (for example, a daily cycle rhythm) which is affected by the body clock, time zones suitable for performing priority actions such as sleeping are decided. Accordingly, the ideal state setting section 104 sets the state of the body clock so as to be synchronized with the biological rhythms, for the priority actions in the predetermined times input by the user.

The ideal state setting section 104 sets a deviation of the phase of the body clock suitable for performing the priority actions from the phase of a standard body clock (a body clock suited to the actual time of the world). The ideal state setting section 104 sets a deviation of the phase of the body clock for each predetermined time. Hereinafter, the unit of time will be in days. However, the unit of time is not limited to this, and may be in minutes, for example.

Figure 5:
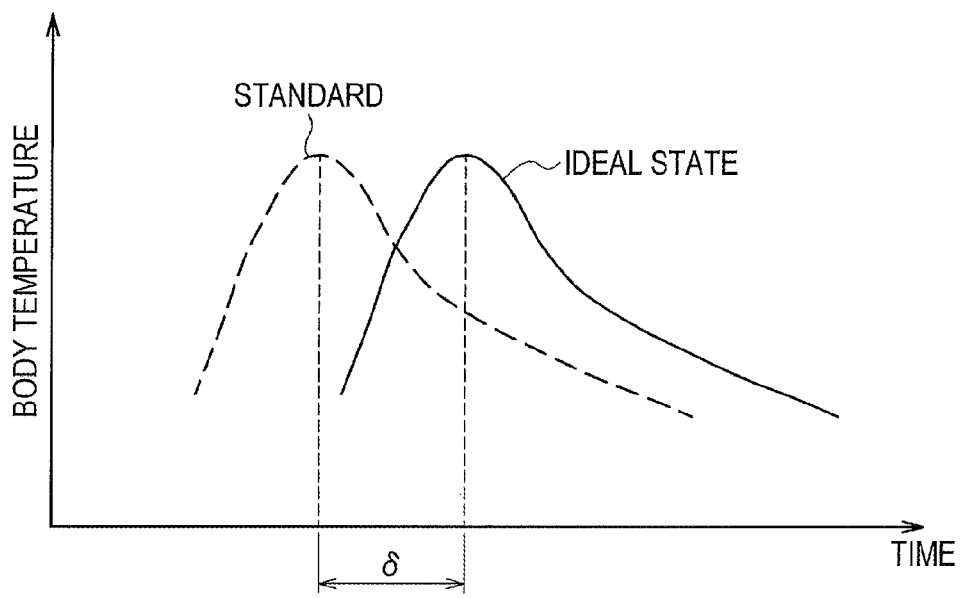
FIG. 5 is a figure which shows an example of a deviation between the state of a standard body clock and the state of an ideal body clock corresponding to a priority action.
Figure 5:
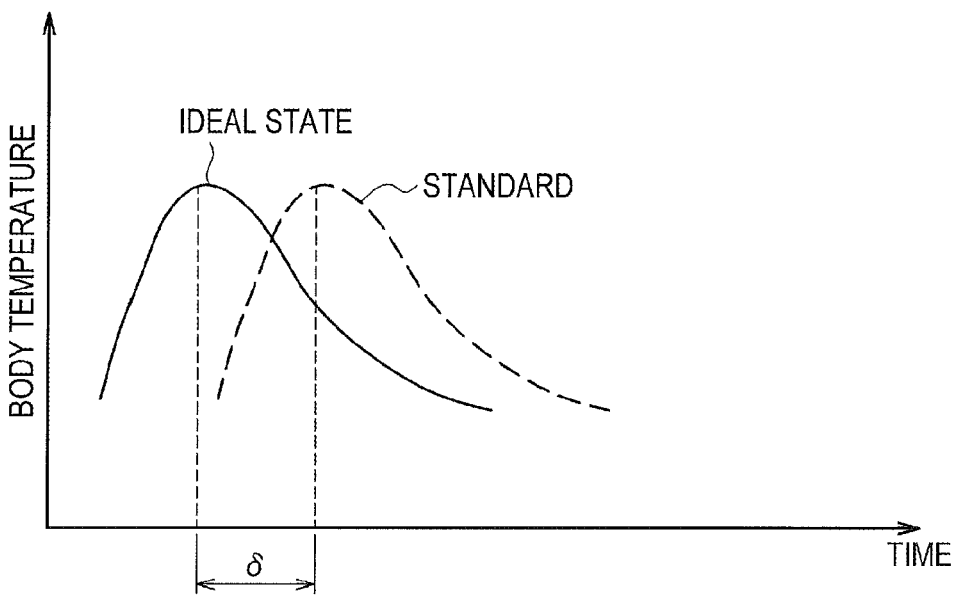

FIG. 5 is a figure which shows an example of a deviation between the state of a standard body clock and the state of an ideal body clock corresponding to a priority action. FIG. 5 shows the deviation of the body clock for one day. In FIG. 5(a), the state of the ideal body clock corresponding to the priority action is ahead of the state of a standard body clock. In FIG. 5(b), the state of the ideal body clock corresponding to the priority action is behind the state of a standard body clock. Also, the deviation of the phase of the body clock is represented by δ.

Figure 6:
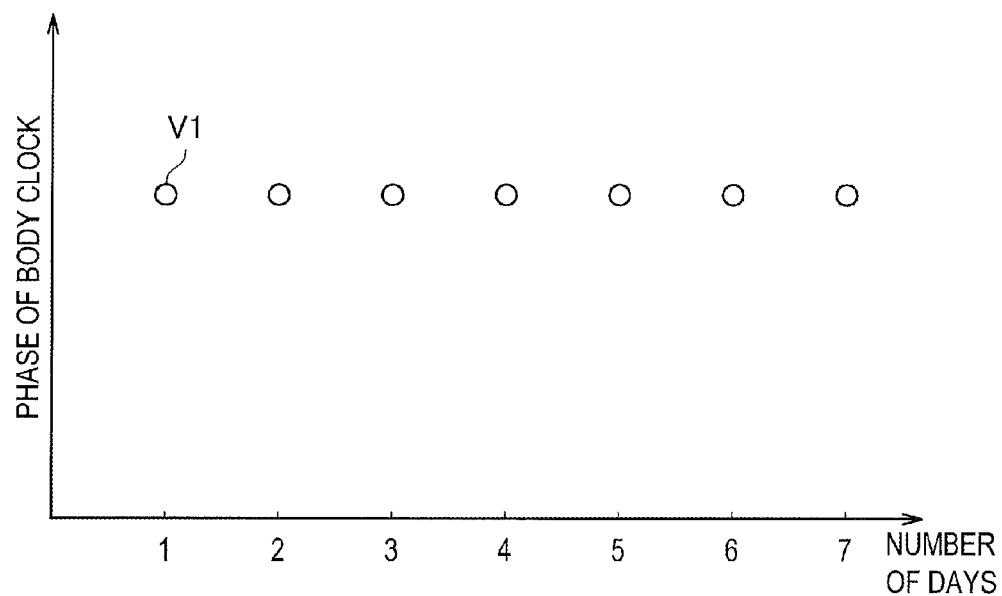
FIG. 6 is a figure which shows an example of a deviation of the phase of an ideal body clock corresponding to a priority action, which has been set at a predetermined time.

The ideal state setting section 104 sets the deviation of the phase of the ideal body clock corresponding to the priority action, which is decided as in FIG. 5, to each of the times as shown in FIG. 6. FIG. 6 is a figure which shows an example of the deviation of the phase of an ideal body clock corresponding to the priority action, which has been set at a predetermined time. In FIG. 6, while the sizes of the deviation of the phase from day 1 to day 7 (the circles shown by V1 in FIG. 6) are the same, the deviation of the phase may fluctuate according to the input priority action. The ideal state setting section 104 outputs setting information such as shown in FIG. 6 to the target value setting section 110.

(Biological Information Acquisition Section 106)

Figure 7:
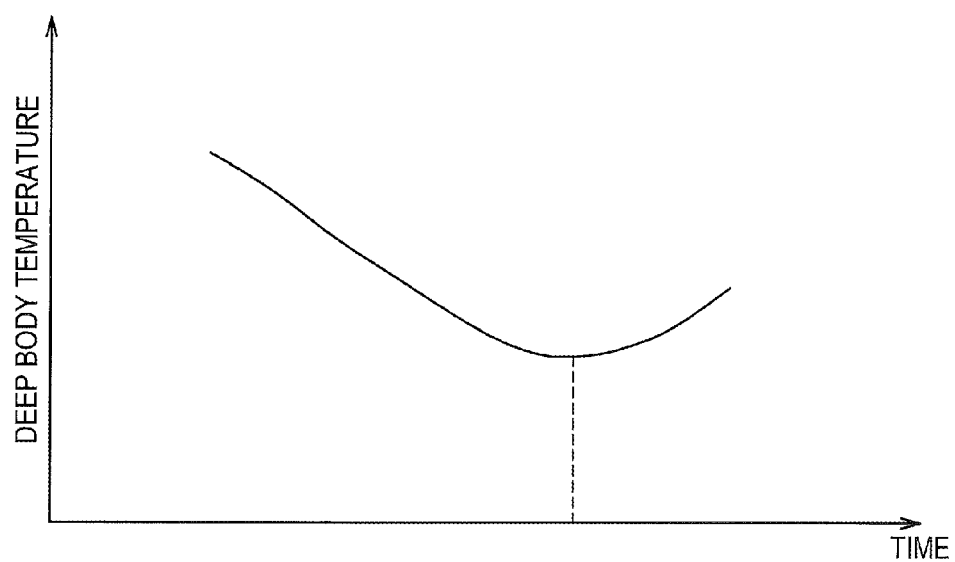
FIG. 7 is a figure which shows an example of the relationship between a deep body temperature and the time.

The biological information acquisition section 106 acquires biological information related to the user's body clock at the present time. It is possible for the biological information to be input by the user in a similar way to that of the priority action information. The biological information acquisition section 106 outputs the acquired biological information to the present state estimation section 108. Here, for example, a deep body temperature such as shown in FIG. 7 is included as the biological information. The deep body temperature may be acquired, for example, by measuring the temperature of the user's ear drum.

FIG. 7 is a figure which shows an example of the relationship between a deep body temperature and the time. Note that in FIG. 7, the fluctuation of the deep body temperature is shown for one day. It is possible to estimate the body clock by observing the time at which the deep body temperature shown in FIG. 7 is at its lowest. Note that the biological information may be information, other than a deep body temperature, related to hair roots, blood, metabolism or the like.

(Present State Estimation Section 108)

Figure 8:
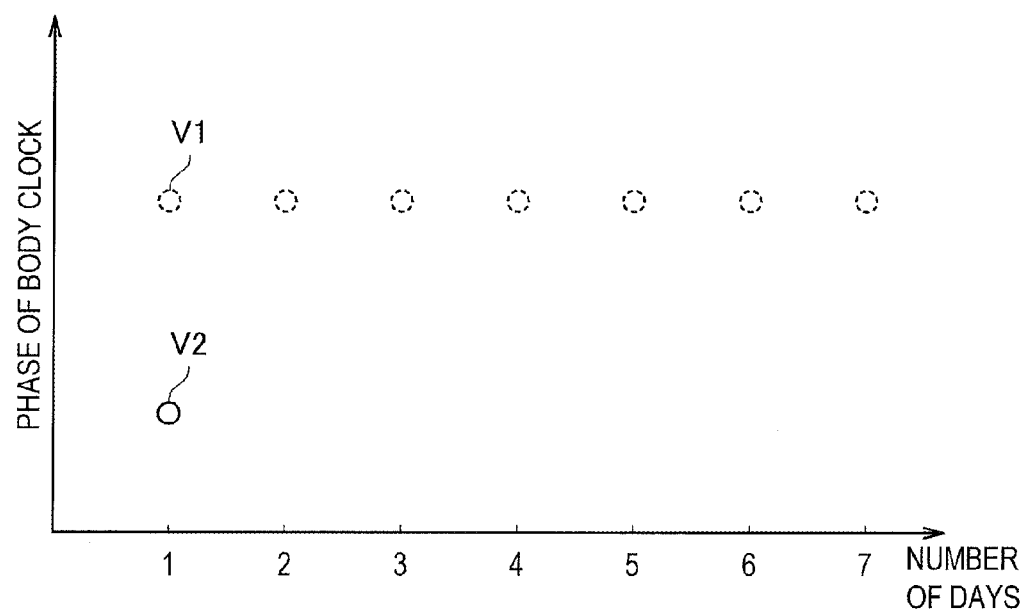
FIG. 8 is a figure which shows an example of a deviation of the phase of the present body clock from that of a standard body clock.

The present state estimation section 108 estimates the state of the user's body clock at the present time, based on the biological information acquired from the biological information acquisition section 106. For example, as shown in FIG. 8, the present state estimation section 108 estimates a deviation of the phase of the body clock (the circle shown by V2 in FIG. 8) at the present time (day 1 shown in FIG. 8) from that of a standard body clock. Note that FIG. 8 is a figure which shows an example of a deviation of the phase of the present body clock from that of a standard body clock. The present state estimation section 108 outputs an estimation result to the target value setting section 110.

(Target Value Setting Section 110)

The target value setting section 110 sets target values for displacing the phase of the body clock of the present state estimated by present state estimation section 108 to the phase of the ideal state set by the ideal state setting section 104. The target value setting section 110 outputs information related to the set target values to the schedule generation section 114.

As can be understood when viewing FIG. 8, the phase of the body clock at present is separated from the phase of the ideal body clock. Accordingly, as shown in FIG. 9, the target value setting section 110 sets the target values of the phase of the body clock from the next time onward (specifically, from day 2 to day 7), so that the body clock of the present time approaches that of the ideal body clock.

Figure 9:
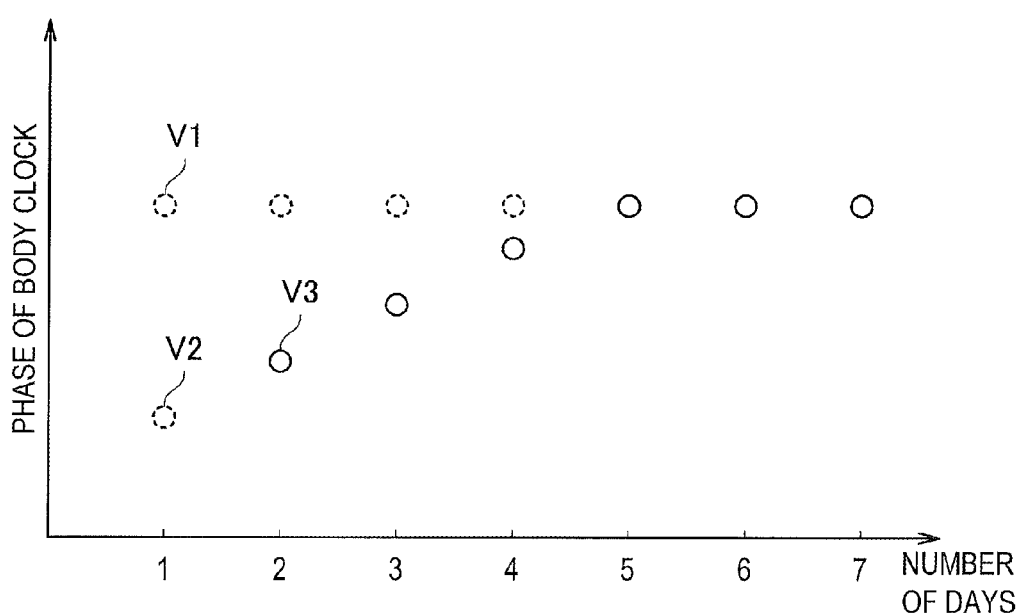
FIG. 9 is a figure which shows an example of target values of the phase of the body clock.

FIG. 9 is a figure which shows an example of target values of the phase of the body clock. Specifically, target values (the circles shown by V3 in FIG. 9) are set so that the phase of the body clock from day 2 onward approaches that of the ideal state (the circles shown by V1 in FIG. 9). In FIG. 9, the target value setting section 110 gradually changes the phase of the body clock between day 2 and day 5.

Note that since there is the possibility of an adverse effect on a user's physical health if the change of the phase of the body clock is too large, the target value setting section 110 may set the target values so that an amount of change of the phase does not exceed a predetermined upper limit for one day. Specifically, the target value setting section 110 sets the target values by referring to information (for example, a phase response curve) related to the control of the body clock stored in a database 120. In this way, the user's body clock can be reasonably adjusted while suppressing any adverse effects on his or her physical health.

(Set Action Information Acquisition Section 112)

The set action information acquisition section 112 acquires set action information related to set actions that are included in the user's schedule and are capable of being set at given times. The set actions are, for example, actions related to actions which have some flexibility in the user's schedule and are interesting for the user. The set action information is acquired, for example, by the user selecting desired set actions from among the set actions displayed on a selection screen of a display section.

FIG. 10 is a figure which shows an example of set actions, which the user has selected on a selection screen, according to the embodiments of the present disclosure. A list of actions capable of being selected as the user's schedule is displayed on the selection screen. In FIG. 10, eating, sports and basking in light are selected by the user as set actions. When set actions are selected, the user may set an order of priority for the set actions.

(Schedule Generation Section 114)

The schedule generation section 114 generates a schedule associating the set actions of the set action information with the times when the set actions are set, based on the target values and the set action information. For example, the schedule generation section 114 generates a one week schedule table in which the times of the set actions have been set (refer to FIG. 11). The schedule generation section 114 outputs information related to the generated schedule to the display control section 116.

The schedule generation section 114 may generate a schedule by referring to information related to the body clock stored in the database 120, in addition to the target values and the set action information. For example, the schedule generation section 114 generates a schedule, based on information which prescribes a change of the phase of the body clock. Here, for example, a phase response curve for the actions can be included as information which prescribes a change of the phase of the body clock. However, it is not limited to a phase response curve, and may be another method.

Further, the schedule generation section 114 generates a schedule, based on information which prescribes times suitable for predetermined actions in the body clock. For example, information for sports that are good for an evening time zone is included as information which prescribes times suitable for predetermined actions in the body clock.

In the case where an order of priority is set for the set actions, the schedule generation section 114 sets the times of the set actions by considering the order of priority. In this way, a schedule can be generated in which the set actions with a high order of priority for the user are executed at a more appropriate time.

(Display Control Section 116)

The display control section 116 displays the state of the body clock in the schedule on a display section 130, based on the target values for displacing the phase of the body clock of the present state to the phase of the ideal state, and the set action information. Specifically, the display control section 116 displays the schedule generated by schedule generation section 114 on the display section 130. The schedule, as shown in FIG. 11, for example, is a one week schedule table in which the times of the set actions have been set.

Figure 11:
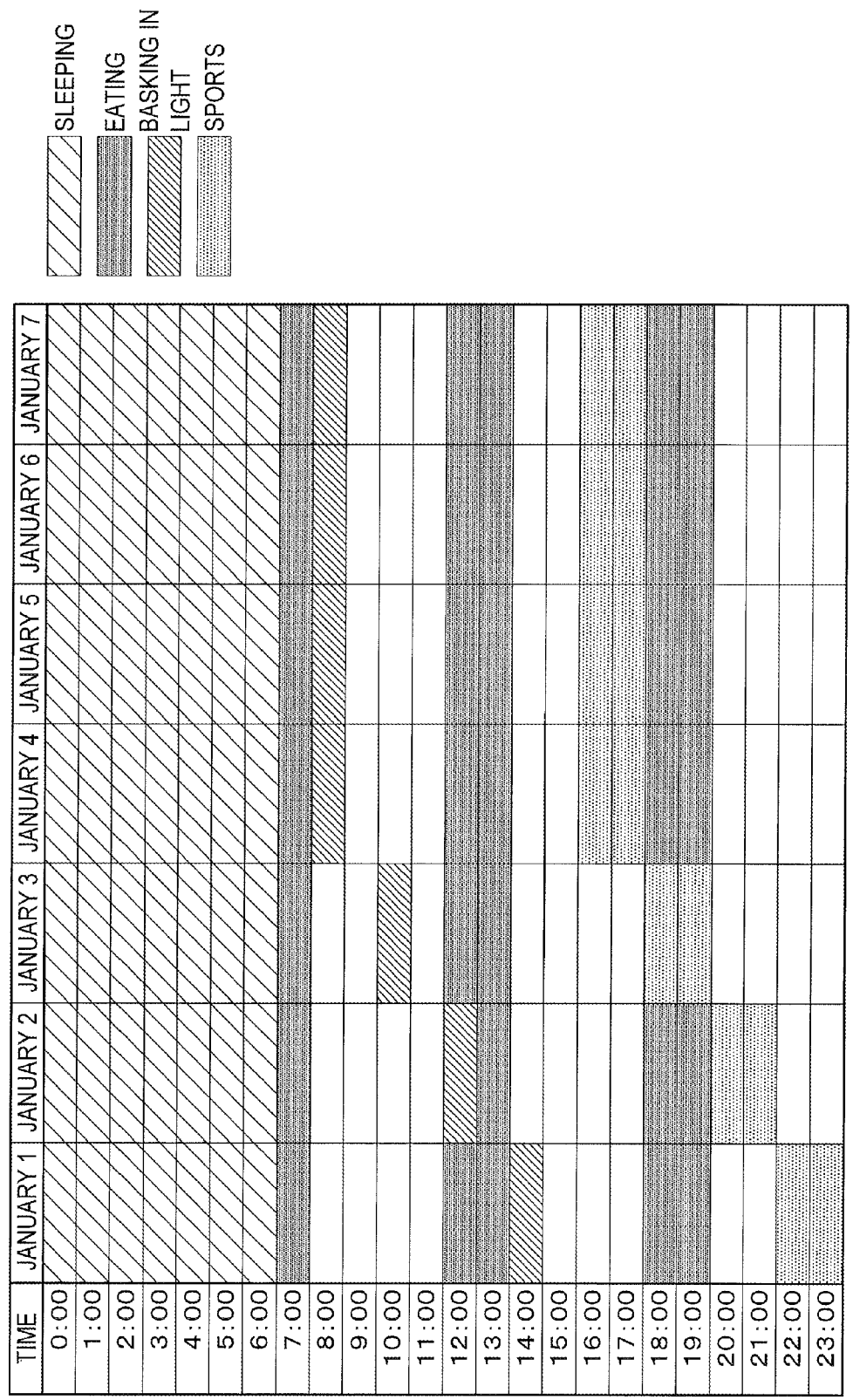
FIG. 11 is a figure which shows an example of a schedule table displayed on the display section 130.

FIG. 11 is a figure which shows an example of a schedule table displayed on the display section 130. A schedule of a priority action (sleeping) and set actions (eating, sports and basking in light) are shown in FIG. 11. The priority action (sleeping) shown in FIG. 11 is set to the times which the user has input (refer to FIG. 2). On the other hand, the set actions (eating, sports and basking in light) have a time set so as to correspond to a change of the phase of the body clock. As can be understood when viewing FIG. 11, the times when being exposed to light or when playing sports are gradually modified so as to gradually change the phase of the body clock.

The user can easily understand the times suitable for performing the set actions, by observing the schedule table shown in FIG. 11. Also, it is possible for the user to shift to an ideal body clock and to perform set actions at a time suitable for his or her biological rhythm, by actually performing the set actions in accordance with the schedule table shown in FIG. 11.

<2. Operation Example of the Information Processing Apparatus>

Figure 12:
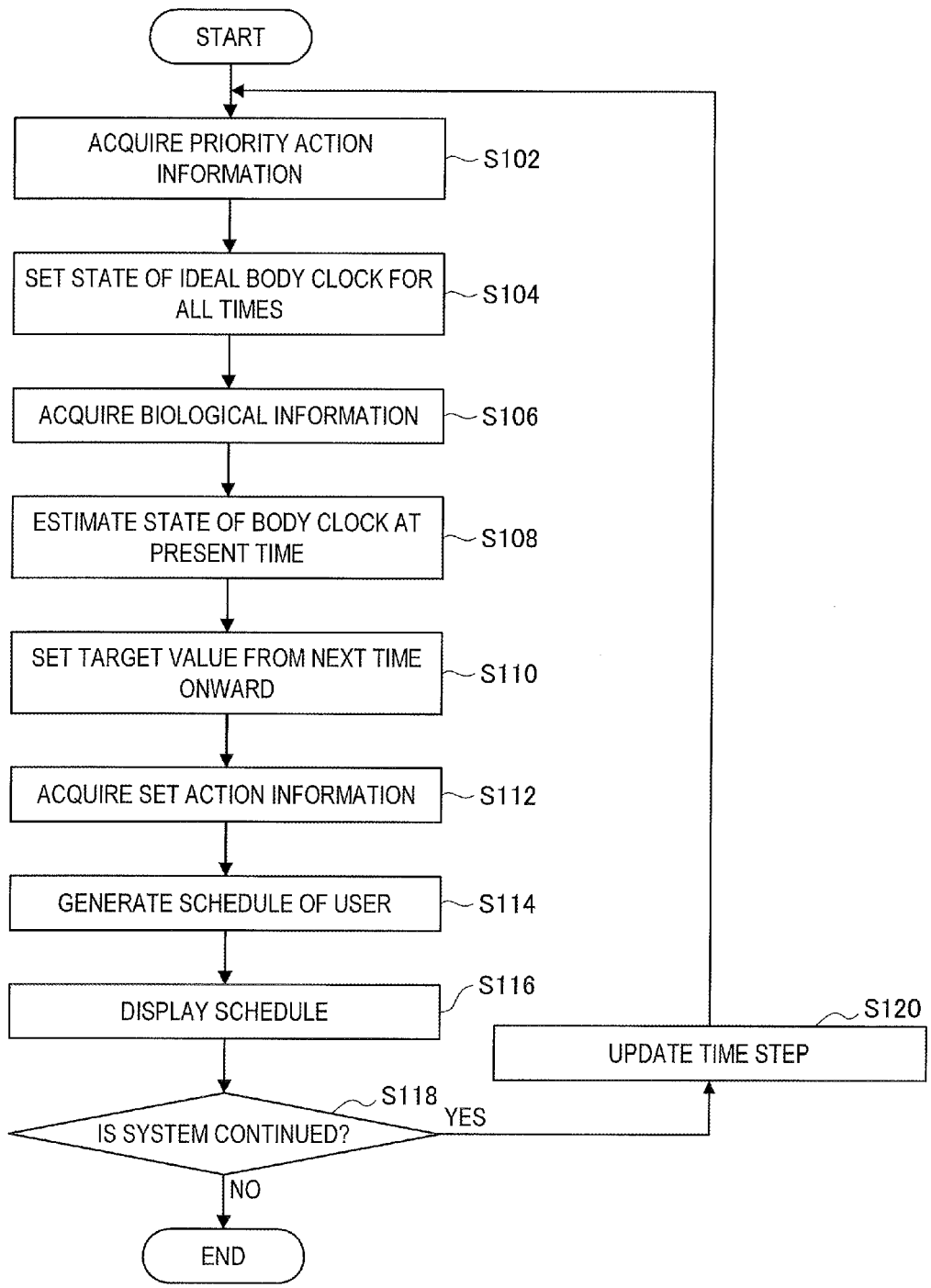
FIG. 12 is a flow chart for describing an operation example of the information processing apparatus 100 according to the embodiments of the present disclosure.

An operation example of the information processing apparatus 100 according to the embodiments of the present disclosure will be described with reference to FIG. 12. FIG. 12 is a flow chart for describing an operation example of the information processing apparatus 100 according to the embodiments of the present disclosure.

First, the priority action information acquisition section 102 acquires priority action information, which has been input by the user and has a high priority for the user (step S102). For example, the priority action information acquisition section 102, as shown in FIGS. 2 to 4, acquires priority action information which associates the priority actions with the times when the priority actions are performed.

Next, the ideal state setting section 104 sets the state of the user's ideal body clock for all the times corresponding to the acquired priority actions (step S104). For example, the ideal state setting section 104, as shown in FIG. 6, sets a deviation of the phase of the body clock for days 1 to 7 corresponding to the priority actions.

Next, the biological information acquisition section 106 acquires biological information for understanding the body clock at the present time (day 1) which has been input by the user (step S106). For example, the biological information acquisition section 106 acquires information related to at least one of a deep body temperature (FIG. 7), blood, or hair roots.

Next, the present state estimation section 108 estimates the state of the user's body clock at the present time (step S108). For example, the present state estimation section 108 estimates the deviation of the phase of the body clock on day 1 (present time), such as shown in FIG. 8.

Next, the target value setting section 110 sets target values of the deviation of the phase of the body clock from the next time onward (step S110). For example, the target value setting section 110, as shown in FIG. 9, sets the target values from day 2 to day 7 of a schedule to which the priority actions have been input.

Next, the set action information acquisition section 112 acquires set action information related to set actions capable of being set at given times (step S112). For example, the set action information acquisition section 112, as shown in FIG. 10, acquires action information related to actions selected by the user, which have some flexibility in the user's schedule and are interesting for the user.

Next, the schedule generation section 114 generates a schedule corresponding to the set actions and the times, based on the target values and set action information (step S114). That is, the schedule generation section 114 generates a schedule which is most suitable for the user's body clock to become the target values, and which makes effective use of the user's body clock.

Next, the display control section 116 displays the generated schedule on the display section 130 (step S116). For example, the display control section 116 displays a one week schedule table, such as shown in FIG. 11, on the display section 130.

Then, in the case where the process is continued from the next time (day 2) onward (step S118: Yes), the time is updated (step S120), and the processes described above (steps S102 to 116) are repeated. On the other hand, in the case where the process is not continued (step S118: No), the operation of the information processing apparatus 100 is completed.

Note that while the display control section 116 displays the schedule screen shown in FIG. 11 on the display section 130 in the above description, it is not limited to this. For example, the display control section 116 may display a 24 hour time screen such as in FIGS. 13 and 14.

Figure 13:
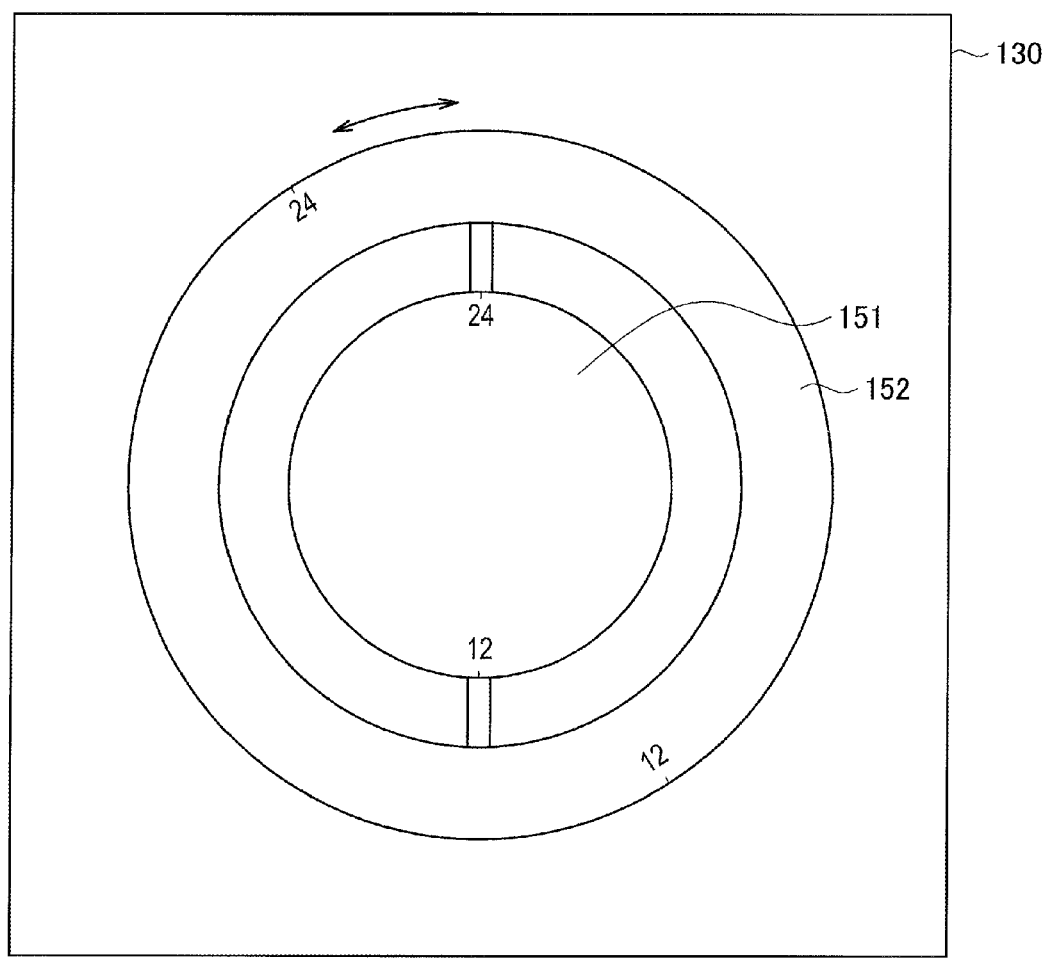
FIG. 13 is a figure which shows an example of the state of a body clock displayed on the display section 130 according to the embodiments of the present disclosure.

FIG. 13 is a figure which shows an example of the state of a body clock displayed on the display section 130 according to the embodiments of the present disclosure. In FIG. 13, the body clock of the present time is shown by the inner circle 151, and the body clock of the ideal state is shown by the outer circular ring 152. FIG. 13 shows the circular ring 152 adapted to rotate with respect to the circle 151, and the deviation between the body clock of the present time and the body clock of the ideal state. Note that the body clock of the present time may be the outer circular ring, and the body clock of the ideal state may be the inner circle.

Figure 14:
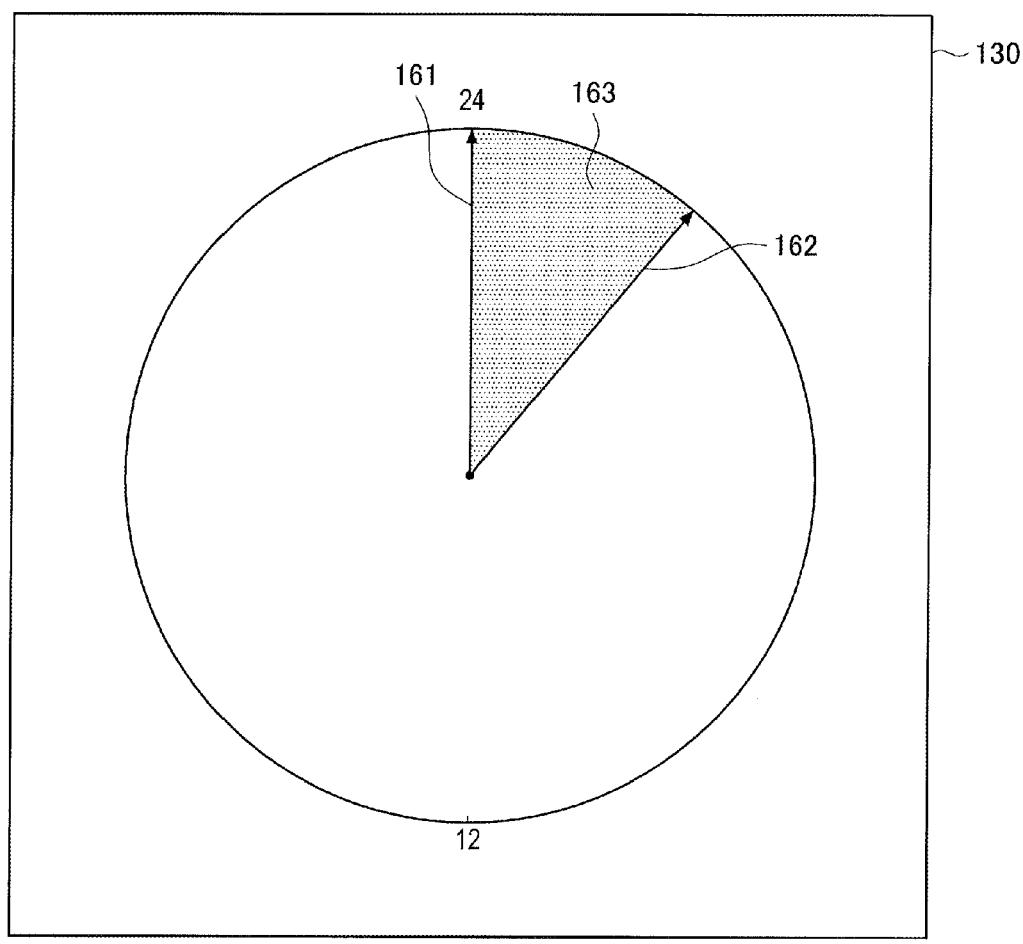
FIG. 14 is a figure which shows an example of the state of a body clock displayed on the display section 130 according to the embodiments of the present disclosure.

FIG. 14 is a figure which shows an example of the state of a body clock displayed on the display section 130 according to the embodiments of the present disclosure. FIG. 14 shows a 12 AM (24:00) hand 161 of the body clock of the ideal state and a 12 AM (24:00) hand 162 of the body clock of the present time. In FIG. 14, the hand 162 moves with respect to the hand 161, and a color corresponding to the degree of deviation of the body clock is shown in the region 163 between the two hands. That is, the color displayed in the region 163 changes according to the degree of deviation.

As shown in FIGS. 13 and 14, the display control section 116 displays the degree of deviation from the ideal state of the body clock in the schedule. By having such a display, the user can easily understand to what degree there is a deviation from the ideal body clock.

Note that the schedule screen shown in FIG. 11 and the time screens shown in FIGS. 13 and 14 may be switched and displayed on the display section 130. In this way, the user can more easily understand visually the state of his or her body clock in the schedule.

<3. Hardware Configuration>

The operations by the above described information processing apparatus 100 are implemented by cooperation between a hardware configuration included in the information processing apparatus 100 and software. Accordingly, hereinafter a hardware configuration of the information process apparatus 100 will be described.

Figure 15:
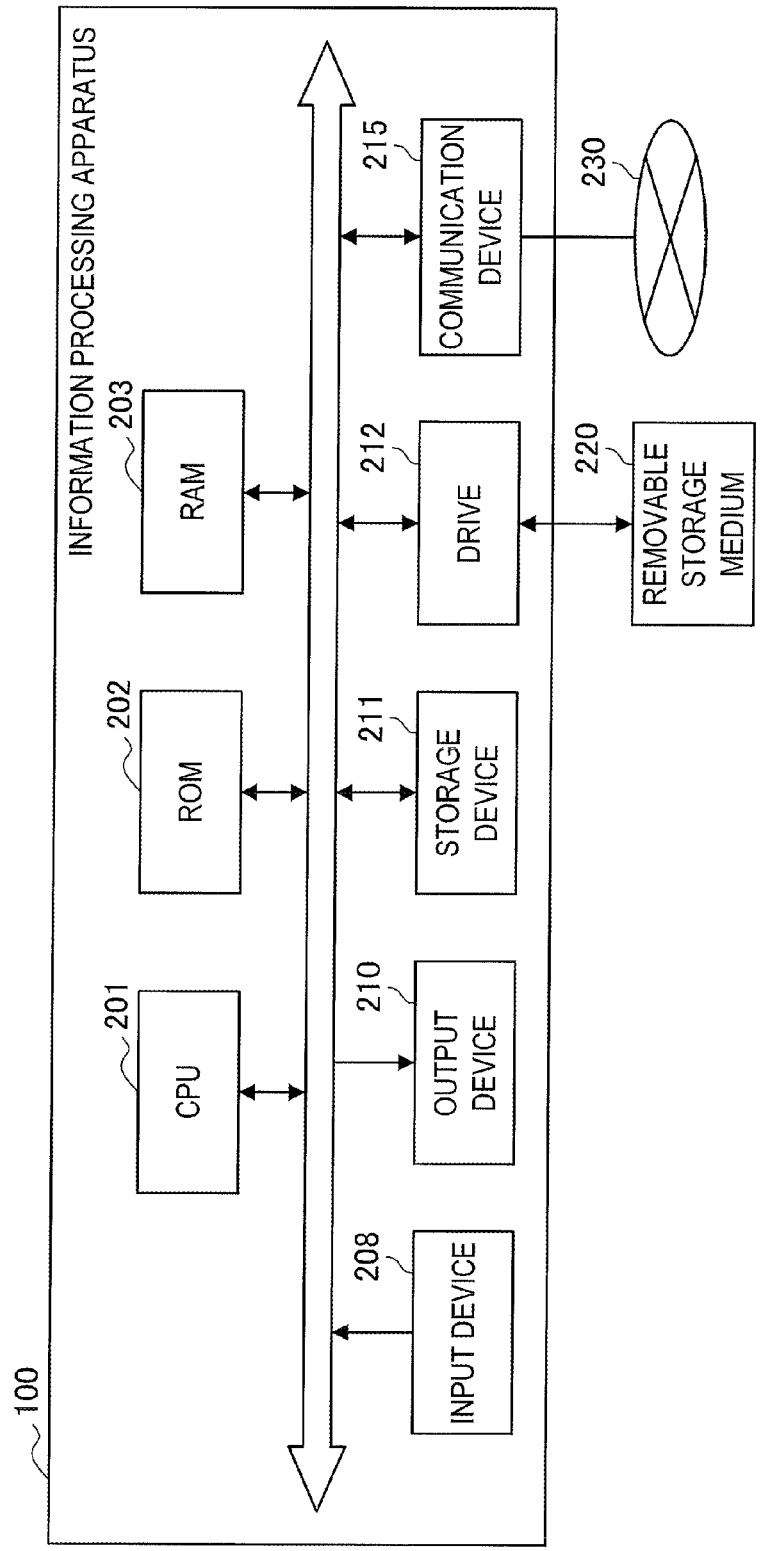
FIG. 15 is an explanatory diagram which shows a hardware configuration example of the information processing apparatus 100.

FIG. 15 is an explanatory diagram which shows a hardware configuration example of the information processing apparatus 100. As shown in FIG. 15, the information processing apparatus 100 includes a CPU (Central Processing Unit) 201, a ROM (Read Only Memory) 202, a RAM (Random Access Memory) 203, an input device 208, an output device 210, a storage device 211, a drive 212, and a communication device 215.

The CPU 201 functions as an operation processing apparatus and a control apparatus, and controls all operations within the image processing apparatus 100, in accordance with various programs. Further, the CPU 201 may be a microprocessor. The ROM 202 stores programs and operation parameters used by the CPU 201. The RAM 203 temporarily stores programs used in the execution of the CPU 201, and parameters which arbitrary change in these executions. These sections are mutually connected by a host bus configured from a CPU bus or the like.

The input device 208 includes an input section, such as a mouse, a keyboard, a touch panel, a button, a microphone, a switch, or a leaver, for a user to input information, and an input control circuit which generates an input signal based on an input by the user, and outputs the input signal to the CPU 201. It is possible for the user of the information processing apparatus 100 to input various data for the information processing apparatus 100 by operating the input device 208, and to display the process operations.

The output device 210 includes, for example, a display device such as a liquid crystal display (LCD) apparatus, an OLED (Organic Light Emitting Diode) apparatus, or a lamp. In addition, the output device 210 includes a voice output device such as a speaker or headphones. For example, the display device displays a picked-up image or a generated image. On the other hand, the voice output device converts voice data and outputs a voice.

The storage device 211 is an apparatus for data storage configured as an example of a storage section of the information processing apparatus 100 according to the present embodiments. The storage device 211 may include a storage medium, a recording apparatus which records data to the storage medium, a reading apparatus which reads data from the storage medium, and an erasure apparatus which erases data recorded in the storage medium. This storage device 211 stores the programs executed by the CPU 201 and the various data.

The drive 212 is a reader/writer for the storage medium, and is built into the information processing apparatus 100 or is externally attached. The drive 212 reads information recorded on a removable storage medium 220, such as a mounted magnetic disk, an optical disk, a magneto-optical disk, or a semiconductor memory, and outputs the information to the RAM 203. Further, the drive 212 can write information to the removable storage medium 220.

The communication device 215 is, for example, a communication interface configured by a communication device for connecting to a network 230. Further, even if the communication device 215 is a communication device adaptive to wireless LAN (Local Area Network) or LTE (Long Term Evolution), the communication device 215 may be a wired communication device which communicates by wires.

Note that the network 230 is a wired or wireless transmission line of information transmitted from an apparatus connected to the network 230. For example, the network 230 may include a public network such as the internet, a telephone network or a satellite communication network, or any of a LAN (Local Area Network), WAN (Wide Area Network) or the like including Ethernet (registered trademark). Further, the network 230 may include a leased line network such as an IP-VPN (Internet Protocol—Virtual Private Network).

<4. Conclusion>

As described above, the information processing apparatus 100 of the present disclosure sets an ideal state of the body clock corresponding to priority actions based on priority action information, and estimates the state of the body clock at the present time based on biological information. Also, the information processing apparatus 100 displays the state of the body clock in a schedule on the display section 130, based on target values for displacing the phase of the body clock of the present state to the phase of the ideal state, and the acquired set action information. Specifically, the information processing apparatus 100 displays either the schedule screen shown in FIG. 11 or the time screens shown in FIGS. 13 and 14.

In this way, for example, the user can easily understand the times suitable for performing set actions, by observing the screen displayed on the display section 130. Further, since the user can easily understand the deviation of his or her body clock at the present time, it becomes easier to adopt a scheme (for example, basking in light) which returns the body clock back to an appropriate state. Therefore, according to the embodiment of the present disclosure, it is possible for a user to appropriately perform actions from a predetermined schedule by effectively utilizing his or her body clock.

It should be understood by those skilled in the art that various modifications, combinations, sub-combinations and alterations may occur depending on design requirements and other factors insofar as they are within the scope of the appended claims or the equivalents thereof.

While the above described embodiments have a portable terminal such as a smart phone or a mobile phone as an information processing apparatus, it is not limited to this. For example, the information processing apparatus may be a PDA, a game machine, a note PC or the like.

Further, while the information processing apparatus 100 sets target values and generates a schedule in the above described embodiments, it is not limited to this. For example, a server capable of communicating with the information processing apparatus 100 through the communication device 215 may set target values and generate a schedule. In such a case, the information processing apparatus 100 displays the schedule, which is generated by the server, on the display section 130.

Further, the steps shown in the flow charts of the above described embodiments may of course be processed in chronological order in accordance with the described order, but they may not necessarily be processed in chronological order, and may be processed individually or in a parallel manner. It is needless to say that, in the case where the steps are processed in chronological order, the order of the steps may be changed appropriately according to the circumstances.

The processes by the information processing apparatus described in the present disclosure may be implemented by using any of the combinations of software, hardware, or software and hardware. Programs included in the software are stored, for example, in advance in a storage medium installed inside or outside of each apparatus. Also, each program is read, for example, to a RAM (Random Access Memory) when executed, and is executed by a processor such as a CPU.

Additionally, the present technology may also be configured as below.

(1) An information processing apparatus, including:
a first information acquisition section which acquires priority action information associating a priority action of a user with a time when the priority action is performed;
a second information acquisition section which acquires biological information related to a body clock of the user at a present time;
a state setting section which sets an ideal state of the body clock corresponding to the priority action, based on the acquired priority action information;
a state estimation section which estimates a present state of the body clock at the present time, based on the acquired biological information;
a third information acquisition section which acquires set action information related to a set action that is included in a schedule of the user and is capable of being set at a given time; and
a display control section which displays a state of the body clock in the schedule on a display section, based on a target value for displacing a phase of the body clock of the present state to a phase of the ideal state and the acquired set action information.

(2) The information processing apparatus according to (1), further including:
a schedule generation section which generates a schedule associating the set action with a time when the set action is set, based on the target value and the set action information,
wherein the display control section displays the generated schedule on the display section.

(3) The information processing apparatus according to (2),
wherein the schedule generation section generates the schedule, based on information which prescribes a displacement of the phase of the body clock.

(4) The information processing apparatus according to (2) or (3),
wherein the schedule generation section generates the schedule, based on information which prescribes a time suitable for a predetermined action in the body clock.

(5) The information processing apparatus according to any one of (2) to (4),
wherein the display control section displays, on the display section, a one week schedule table in which the time of the set action has been set.

(6) The information processing apparatus according to any one of (1) to (5),
wherein the display control section displays a degree of deviation from the ideal state of the body clock in the schedule.

(7) The information processing apparatus according to any one of (1) to (6), further including:
a target value setting section which sets the target value for displacing the phase of the body clock of the present state to the phase of the ideal state.

(8) The information processing apparatus according to any one of (1) to (7),
wherein the biological information is information related to at least one of a deep body temperature, blood, or a hair root of the user.

(9) An information processing method, including:
acquiring priority action information associating a priority action of a user with a time when the priority action is performed;
acquiring biological information related to a body clock of the user at a present time;
setting an ideal state of the body clock corresponding to the priority action, based on the acquired priority action information;
estimating a present state of the body clock at the present time, based on the acquired biological information;
acquiring set action information related to a set action that is included in a schedule of the user and is capable of being set at a given time; and
displaying a state of the body clock in the schedule on a display section, based on a target value for displacing a phase of the body clock of the present state to a phase of the ideal state and the acquired set action information.

(10) A program for causing a computer to execute:
acquiring priority action information associating a priority action of a user with a time when the priority action is performed;
acquiring biological information related to a body clock of the user at a present time;
setting an ideal state of the body clock corresponding to the priority action, based on the acquired priority action information;
estimating a present state of the body clock at the present time, based on the acquired biological information;
acquiring set action information related to a set action that is included in a schedule of the user and is capable of being set at a given time; and
displaying a state of the body clock in the schedule on a display section, based on a target value for displacing a phase of the body clock of the present state to a phase of the ideal state and the acquired set action information.

The present disclosure contains subject matter related to that disclosed in Japanese Priority Patent Application JP 2012-080995 filed in the Japan Patent Office on Mar. 30, 2012, the entire content of which is hereby incorporated by reference.

What is claimed is:
1. An information processing apparatus, comprising:
at least one processor; and
at least one non-transitory computer-readable storage medium having encoded thereon executable instructions that, when executed by the at least one processor, cause the at least one processor to carry out a method comprising:
acquiring priority action information indicating a priority action and a time that a user intends to perform the priority action;
acquiring biological information of the user;
setting a target state of a body clock of the user for the time that the user intends to perform the priority action, based at least in part on the priority action information;
estimating a present state of the body clock of the user at a time that the biological information for the user was collected, based at least in part on the biological information;

displaying a list of a plurality of actions to be performed by the user, wherein one or more actions, other than the priority action, are selected by the user among the displayed list of the plurality of actions, and wherein each action of the one or more actions selected by the user among the displayed list of the plurality of actions, is included in a schedule of the user;

determining action information related to the selected one or more actions that are to be performed by the user between a current time and the time that the user intends to perform the priority action;

generating, based at least in part on the present state of the body clock of the user, the schedule prescribing a time at which to schedule the selected one or more actions to adjust a phase of the body clock such that a state of the body clock at the time that the user intends to perform the priority action matches the target state; and outputting, for display, the schedule indicating that the selected one or more actions are to be performed at the prescribed time.

2. The information processing apparatus according to claim 1, wherein generating the schedule is based at least in part on information which prescribes a displacement of phase of the body clock.

3. The information processing apparatus according to claim 1, wherein generating the schedule is based at least in part on information which prescribes a suitable body clock state for a predetermined action.

4. The information processing apparatus according to claim 1, wherein outputting the schedule for display comprises outputting a one week schedule table indicating that the selected one or more actions are to be performed at the prescribed time.

5. The information processing apparatus according to claim 1, wherein the method further comprises:
outputting for display in the schedule a predicted degree of deviation of a state of the body clock of the user at a time from the target state of the body clock.

6. The information processing apparatus according to claim 1, wherein the method further comprises:
setting a target value so as to displace the phase of the body clock of the present state to the phase of the target state.

7. The information processing apparatus according to claim 1, wherein the biological information is information related to at least one of a deep body temperature, blood, or a hair root of the user.

8. The information processing apparatus of claim 1, wherein setting the target state of the body clock for the time that the user intends to perform the priority action comprises setting an ideal state for the priority action.

9. The information processing apparatus according to claim 1, wherein the prescribed time at which to schedule the selected one or more actions is based on priority order information associated with the selected one or more actions.

10. The information processing apparatus according to claim 1, wherein the action information is determined based on a priority order, provided by the user, associated with each of the selected one or more actions.

11. The information processing apparatus according to claim 1, wherein in the displayed schedule, a time at which the priority action is to be performed corresponds to the time indicated by the acquired priority action information, that the user intends to perform the priority action, based at least in part on the priority action information.

12. An information processing method, comprising:
in at least one processor:
acquiring priority action information indicating a priority action and a time that a user intends to perform the priority action;
acquiring biological information of the user;
setting a target state of a body clock of the user for the time that the user intends to perform the priority action, based at least in part on the priority action information;
estimating a present state of the body clock of the user at a time that the biological information for the user was collected, based at least in part on the biological information;
displaying a list of a plurality of actions to be performed by the user, wherein one or more actions, other than the priority action, are selected by the user among the displayed list of the plurality of actions, and wherein each action of the one or more actions selected by the user among the displayed list of the plurality of actions, is included in a schedule of the user;
determining action information related to the selected one or more actions that are to be performed by the user between a current time and the time that the user intends to perform the priority action;
generating, based at least in part on the present state of the body clock of the user, the schedule prescribing a time at which to schedule the selected one or more actions to adjust a phase of the body clock such that a state of the body clock at the time that the user intends to perform the priority action matches the target state; and
outputting, for display, the schedule indicating that the selected one or more actions are to be performed at the prescribed time.

13. At least one non-transitory computer-readable storage medium having encoded thereon executable instructions that, when executed by at least one computing device, cause the at least one computing device to carry out a method comprising:
acquiring priority action information indicating a priority action and a time that a user intends to perform the priority action;
acquiring biological information of the user;
setting a target state of a body clock of the user for the time that the user intends to perform the priority action, based at least in part on the priority action information;
estimating a present state of the body clock of the user at a time that the biological information for the user was collected, based at least in part on the biological information;
displaying a list of a plurality of actions to be performed by the user, wherein one or more actions, other than the priority action, are selected by the user among the displayed list of the plurality of actions, and wherein each action of the one or more actions selected by the user among the displayed list of the plurality of actions, is included in a schedule of the user;
determining action information related to the selected one or more actions that are to be performed by the user between a current time and the time that the user intends to perform the priority action;
generating, based at least in part on the present state of the body clock of the user, the schedule prescribing a time at which to schedule the selected one or more actions to adjust a phase of the body clock such that a state of the body clock at the time that the user intends to perform the priority action matches the target state; and outputting, for display, the schedule indicating that the selected one or more actions are to be performed at the prescribed time.

\* \* \* \* \*